United States Patent
Kim et al.

(10) Patent No.: US 12,310,549 B1
(45) Date of Patent: May 27, 2025

(54) METHOD OF DETECTING LESIONS IN ENDOSCOPIC IMAGES, AND METHOD AND COMPUTING DEVICE FOR TRAINING ARTIFICIAL NEURAL NETWORK MODEL THAT PERFORMS THE SAME

(71) Applicant: MedInTech Inc., Seoul (KR)

(72) Inventors: Myungjoon Kim, Gwacheon (KR); Seokho Cho, Seoul (KR); Donghyeok Kim, Seoul (KR)

(73) Assignee: MedInTech Inc., Seoul (KR)

( * ) Notice: Subject to any disclaimer, the term of this patent is extended or adjusted under 35 U.S.C. 154(b) by 0 days.

(21) Appl. No.: 18/953,345

(22) Filed: Nov. 20, 2024

(30) Foreign Application Priority Data

Nov. 21, 2023 (KR) .................. 10-2023-0162014

(51) Int. Cl.
  *G06T 7/00* (2017.01)
  *A61B 1/00* (2006.01)

(52) U.S. Cl.
  CPC ...... *A61B 1/000096* (2022.02); *G06T 7/0012* (2013.01); *A61B 2576/00* (2013.01); *G06T 2207/10068* (2013.01); *G06T 2207/20081* (2013.01); *G06T 2207/20084* (2013.01); *G06T 2207/30096* (2013.01)

(58) Field of Classification Search
  CPC .......... A61B 1/000096; A61B 2576/00; G06T 7/0012; G06T 2207/10068; G06T 2207/20081; G06T 2207/20084; G06T 2207/30096
  See application file for complete search history.

(56) References Cited

U.S. PATENT DOCUMENTS

| | | | | |
|---|---|---|---|---|
| 2012/0316421 | A1* | 12/2012 | Kumar | A61B 1/000096 600/407 |
| 2021/0133976 | A1* | 5/2021 | Carmi | G16H 30/20 |
| 2022/0031227 | A1* | 2/2022 | Cho | G06V 10/82 |
| 2023/0047100 | A1* | 2/2023 | Arcadu | A61B 1/31 |
| 2023/0162356 | A1* | 5/2023 | Horiuchi | A61B 1/00055 382/128 |
| 2023/0410295 | A1* | 12/2023 | Sousa Ferreira | G06N 3/096 |
| 2024/0013377 | A1* | 1/2024 | Sousa Ferreira | G06T 7/0012 |
| 2024/0016366 | A1* | 1/2024 | Jeong | G16H 40/63 |
| 2024/0037733 | A1* | 2/2024 | Bang | G06V 10/82 |
| 2024/0249409 | A1* | 7/2024 | Mayer | G06N 3/0464 |
| 2024/0354949 | A1* | 10/2024 | Sousa Ferreira | G06N 3/091 |

(Continued)

FOREIGN PATENT DOCUMENTS

| | | |
|---|---|---|
| KR | 10-2021-0109866 | 9/2021 |
| KR | 10-2021-0134121 | 11/2021 |
| KR | 10-2344585 B1 | 12/2021 |

(Continued)

*Primary Examiner* — Van D Huynh
(74) *Attorney, Agent, or Firm* — Harvest IP Law, LLP

(57) ABSTRACT

The present disclosure is directed to a method of training an artificial neural network model for detecting lesions in endoscopic images that is performed by a computing device including at least one processor. The method includes: generating training data including labels for lesions based on endoscopic images with characteristics of regions where the endoscopic images are captured and characteristics of the lesions taken into consideration; and training an artificial neural network model to detect the lesions in endoscopic images based on the training data.

10 Claims, 4 Drawing Sheets

(56) References Cited

U.S. PATENT DOCUMENTS

2024/0394890 A1* 11/2024 Zeng .................... G06T 7/11
2024/0420330 A1* 12/2024 Lee ..................... G06T 7/0012

FOREIGN PATENT DOCUMENTS

| KR | 10-2022-0068458   | 5/2022 |
| KR | 10-2022-0075119   | 6/2022 |
| KR | 10-2022-0090840   | 6/2022 |
| KR | 10-2022-0096453 A | 7/2022 |
| KR | 10-2022-0114329   | 8/2022 |
| KR | 10-2022-0121956 A | 9/2022 |

* cited by examiner

METHOD OF DETECTING LESIONS IN ENDOSCOPIC IMAGES, AND METHOD AND COMPUTING DEVICE FOR TRAINING ARTIFICIAL NEURAL NETWORK MODEL THAT PERFORMS THE SAME

CROSS-REFERENCE TO RELATED APPLICATION

This application claims the benefit of Korean Patent Application No. 10-2023-0162014 filed on Nov. 21, 2023, which is hereby incorporated by reference herein in its entirety.

BACKGROUND

1. Technical Field

The present disclosure relates to technology that trains an artificial neural network model for detecting lesions in endoscopic images and detects lesions in endoscopic images by using the trained artificial neural network model.

2. Description of the Related Art

Endoscopes collectively refer to medical devices that allow a scope to be inserted into the human body and a user to observe an organ without surgery or autopsy. Endoscopes allow a scope to be inserted into the body, radiate light, and visualize the light reflected from the surface of the inner wall of the body. Endoscopes are classified according to their purpose and target body part, and may be basically classified into rigid endoscopes, in which an endoscopic tube is made of metal, and flexible endoscopes, which are represented by digestive endoscopes.

The inside of a digestive organ into which a flexible endoscope is inserted corresponds to a considerably fragile tissue, and has an irregular shape. Furthermore, the shape of the inside of the digestive organ varies depending on the patient, so that the process of inserting the endoscope may not be easy even for experienced medical professionals. In this situation, medical professionals need to concentrate their attention to safely insert an endoscope and search for a lesion, so that the fatigue of the medical professions increases significantly when endoscopic procedures are performed repeatedly.

Therefore, for the convenience of medical professions, research is being conducted into technology for searching for lesions in endoscopic images. In particular, object recognition models that detect various features in images are being actively applied to the field of endoscopic imaging. Object recognition artificial neural network models are trained to perform the region proposal operation of rapidly finding the region where an object is likely to be present and the classification operation of classifying a specific object.

Meanwhile, endoscopic images contain various types of noise due to the nature of the environment in which they are taken in the insides of digestive organs in the form of narrow tubes, and the shapes of endoscopic images change significantly depending on the movement of the scope. Furthermore, the shapes of lesions to be recognized are considerably diverse, and therefore, it is difficult to increase the sensitivity and accuracy of artificial neural network models that detect them.

Related Art Literature

Korean Patent No. 10-2344585 (published on Dec. 24, 2021)

SUMMARY

The present disclosure has been contrived in response to the above-described background technology, and is directed to a method of detecting lesions in endoscopic images by preparing training data for an artificial neural network model with the characteristics of regions where endoscopic images are captured and the characteristics of lesions taken into consideration, and a method and computing device for training an artificial neural network model that performs the same.

However, the objects to be accomplished by the present disclosure are not limited to the object mentioned above, and other objects not mentioned may be clearly understood based on the following description.

According to one embodiment of the present disclosure for achieving the above-described object, there is disclosed a method of training an artificial neural network model for detecting lesions in endoscopic images that is performed by a computing device including at least one processor. The method includes: generating training data including labels for lesions based on endoscopic images with characteristics of regions where the endoscopic images are captured and characteristics of the lesions taken into consideration; and training an artificial neural network model to detect the lesions in endoscopic images based on the training data.

Alternatively, the training data may contain lesion training data including each of the lesions and normal training data not including the lesion at a specific ratio; and the ratio may be determined according to clinical characteristics of the lesion.

Alternatively, the clinical characteristics of the lesion may include the frequency of occurrence or type of the lesion.

Alternatively, the lesion training data may be generated an augmentation technique that maintains image by characteristics of the lesion.

Alternatively, the training data may include learning data, verification data, and evaluation data, and the learning data, the verification data, and the evaluation data may be constructed based on patient information from which the training data is obtained.

Alternatively, training the artificial neural network model may include assigning weights so that inference results of the artificial neural network model are determined by reflecting clinical characteristics of the lesions therein, Alternatively, assigning weights may the include assigning higher weights to training data including a lesion with higher reading difficulty.

Alternatively, the type of loss function of the artificial neural network model is determined according to clinical or image characteristics of the lesions.

Alternatively, the loss function of the artificial neural network model may include a loss function having a distance IoU (DIoU) structure.

Alternatively, the artificial neural network model may be trained to detect images not including any one of the lesions in endoscopic images based on the training data.

Alternatively, a loss function of the artificial neural network model may be determined based on a loss function adapted to detect the lesions and a loss function adapted to detect images not including any one of the lesions.

According to one embodiment of the present disclosure for achieving the above-described object, there is disclosed a method of detecting lesions in endoscopic images that is performed by a computing device including at least one processor. The method includes detecting lesions or images not including any one of the lesions in endoscopic images by using an artificial neural network model trained with training data that is generated based on at least one of characteristics of regions where endoscopic images are captured, clinical characteristics of the lesions, and image characteristics of the lesions.

According to one embodiment of the present disclosure for achieving the above-described object, there is disclosed a computing device for training an artificial neural network model for detecting lesions in endoscopic images. The computing device includes a processor including at least one core, and memory including program codes executable on the processor, and the processor generates training data including labels for lesions based on endoscopic images with characteristics of regions where the endoscopic images are captured and characteristics of the lesions taken into consideration, and trains an artificial neural network model to detect the lesions in endoscopic images based on the training data.

The present disclosure prepares training data for an artificial neural network model that detects lesions by taking into consideration the clinical characteristics of the lesions, thereby achieving a higher level of sensitivity and accuracy required in the medical field than an artificial neural network model that is simply trained based on morphological characteristics.

In addition, the present disclosure detects endoscopic images not including a lesion by taking into consideration the actual endoscopic procedure situation in which the rate at which endoscopic images not including a lesion are obtained is high, thereby increasing the accuracy of inference.

BRIEF DESCRIPTION OF THE DRAWINGS

The above and other objects, features, and advantages of the present invention will be more clearly understood from the following detailed description taken in conjunction with the accompanying drawings, in which.

DETAILED DESCRIPTION

Figure 1:
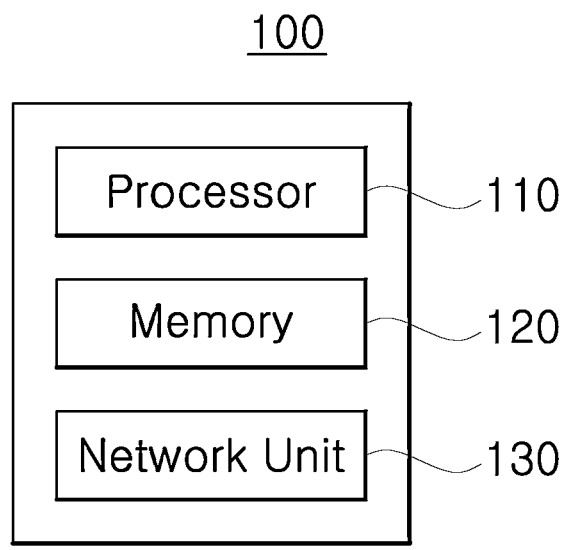
FIG. 1 is a block diagram of a computing device according to one embodiment of the present disclosure.

Embodiments of the present disclosure will be described in detail below with reference to the accompanying drawings so that those having ordinary skill in the art of the present disclosure (hereinafter referred to as those skilled in the art) can easily implement the present disclosure. The embodiments presented in the present disclosure are provided to enable those skilled in the art to use or practice the content of the present disclosure. Accordingly, various modifications to embodiments of the present disclosure will be apparent to those skilled in the art. That is, the present disclosure may be implemented in various different forms and is not limited to the following embodiments.

The same or similar reference numerals denote the same or similar components throughout the specification of the present disclosure. Additionally, in order to clearly describe the present disclosure, reference numerals for parts that are not related to the description of the present disclosure may be omitted in the drawings.

The term "or" used herein is intended not to mean an exclusive "or" but to mean an inclusive "or." That is, unless otherwise specified herein or the meaning is not clear from the context, the clause "X uses A or B" should be understood to mean one of the natural inclusive substitutions. For example, unless otherwise specified herein or the meaning is not clear from the context, the clause "X uses A or B" may be interpreted as any one of a case where X uses A, a case where X uses B, and a case where X uses both A and B.

The term "at least one of A and B" used herein should be interpreted to refer to all of A, B, and a combination of A and B.

The term "and/or" used herein should be understood to refer to and include all possible combinations of one or more of listed related concepts.

The terms "include" and/or "including" used herein should be understood to mean that specific features and/or components are present. However, the terms "include" and/or "including" should be understood as not excluding the presence or addition of one or more other features, one or more other components, and/or combinations thereof.

Unless otherwise specified herein or unless the context clearly indicates a singular form, the singular form should generally be construed to include "one or more."

The term "N-th (N is a natural number)" used herein can be understood as an expression used to distinguish the components of the present disclosure according to a predetermined criterion such as a functional perspective, a structural perspective, or the convenience of description. For example, in the present disclosure, components performing different functional roles may be distinguished as a first component or a second component. However, components that are substantially the same within the technical spirit of the present disclosure but should be distinguished for the convenience of description may also be distinguished as a first component or a second component.

The term "model" used herein may be understood as a system implemented using mathematical concepts and language to solve a specific problem, a set of software units intended to solve a specific problem, or an abstract model for a process intended to solve a specific problem. For example, a neural network "model" may refer to an overall system implemented as a neural network that is provided with problem-solving capabilities through training. In this case, the neural network may be provided with problem-solving capabilities by optimizing parameters connecting nodes or neurons through training. The neural network "model" may include a single neural network, or a neural network set in which multiple neural networks are combined together.

The foregoing descriptions of the terms are intended to help understand the present disclosure. Accordingly, it should be noted that unless the above-described terms are explicitly described as limiting the content of the present disclosure, the terms in the content of the present disclosure are not used in the sense of limiting the technical spirit of the present disclosure.

FIG. 1 is a block diagram of a computing device 100 according to one embodiment of the present disclosure.

The computing device 100 according to the one embodiment of the present disclosure may be a hardware device or part of a hardware device that performs the comprehensive processing and computation of data, or may be a software-based computing environment that is connected to a communication network. For example, the computing device 100 may be a server that performs an intensive data processing function and shares resources, or may be a client that shares resources through interaction with a server. Furthermore, the computing device 100 may be a cloud system in which a plurality of servers and clients interact with each other and comprehensively process data. Since the above descriptions are only examples related to the type of computing device 100, the type of computing device 100 may be configured in various manners within a range understandable to those skilled in the art based on the content of the present disclosure.

The computing device 100 may be connected with an endoscope device for obtaining various types of information including medical images of the inside of the human body via a wired/wireless connection. That is, the computing device 100 may receive information required for performing the operations to be described below from the endoscope device through, for example, a network unit, and may provide generated information to the endoscope device. As an example, the computing device 100 may receive endoscopic images for the generation of training data from the endoscope device. Furthermore, the computing device 100 may receive input data for the inference of a trained artificial neural network model from the endoscope device, and may provide inference results to the endoscope device. Meanwhile, the computing device 100 may also perform the above-described operations on a server of a hospital that includes a plurality of endoscope devices. Meanwhile, the computing device 100 may be implemented as a component inside the endoscope device. In this case, the computing device 100 may perform a role corresponding to the role of the control unit of the endoscope device.

Referring to FIG. 1, the computing device 100 according to the one embodiment of the present disclosure may include a processor 110, memory 120, and a network unit 130. However, FIG. 1 shows only an example, and the computing device 100 may include other components for implementing a computing environment. Furthermore, only some of the components disclosed above may be included in the computing device 100.

The processor 110 according to an embodiment of the present disclosure may be understood as a constituent unit including hardware and/or software for performing computing operation. For example, the processor 110 may read a computer program and perform data processing for machine learning. The processor 110 may process computational processes such as the processing of input data for machine learning, the extraction of features for machine learning, and the calculation of errors based on backpropagation. The processor 110 for performing such data processing may include a central processing unit (CPU), a general purpose graphics processing unit (GPGPU), a tensor processing unit (TPU), an application specific integrated circuit (ASIC), or a field programmable gate array (FPGA). Since the types of processor 110 described above are only examples, the type of processor 110 may be configured in various manners within a range understandable to those skilled in the art based on the content of the present disclosure.

The processor 110 may perform a series of operations for training an artificial neural network model that detects lesions included in endoscopic images. In this case, the processor 110 may generate training data by reflecting the clinical characteristics of endoscopic images therein. More specifically, the processor 110 may generate training data including labels for lesions based on endoscopic images with the characteristics of the regions where the endoscopic images are captured and the characteristics of the lesions taken into consideration. Furthermore, the training data may include endoscopic images that do not include a lesion. Moreover, the processor 110 may train an artificial neural network model based on the training data to detect lesions in endoscopic images.

Therefore, by preparing training data with the types, frequencies of occurrence, risks, shapes, and like of lesions taken into consideration, the present disclosure may achieve a higher level of sensitivity and accuracy required in the medical field than an artificial neural network model that is trained simply based on morphological characteristics.

Furthermore, to ensure speed and reliability that can be used in an actual endoscopic procedure beyond the simple detection of a lesion using a still image, the processor 110 may design the structure of an artificial neural network model and train the artificial neural network model. More specifically, the processor 110 may train the artificial neural network model to perform the operation of detecting lesions and the operation of detecting images not including a lesion. In an actual endoscopic procedure situation, the ratio of endoscopic images that do not include lesions is high, so that inference accuracy can be increased by detecting endoscopic images that do not include lesions as well as endoscopic images that include lesions.

The processor 110 may detect lesions or images not including a lesion in endoscopic images by using the artificial neural network model trained as described above.

The memory 120 according to an embodiment of the present disclosure may be understood as a constituent unit including hardware and/or software for storing and managing data that is processed in the computing device 100. That is, the memory 120 may store any type of data generated or determined by the processor 110 and any type of data received by the network unit 130. For example, the memory 120 may include at least one type of storage medium of a flash memory type, hard disk type, multimedia card micro type, and card type memory, random access memory (RAM), static random access memory (SRAM), read-only memory (ROM), electrically erasable programmable read-only memory (EEPROM), programmable read-only memory (PROM), magnetic memory, a magnetic disk, and an optical disk. Furthermore, the memory 120 may include a database system that controls and manages data in a predetermined system. Since the types of memory 120 described above are only examples, the type of memory 120 may be configured in various manners within a range understandable to those skilled in the art based on the content of the present disclosure.

The memory 120 may include endoscopic images, training data generated based on the endoscopic images, and program codes executable on the processor 110.

The network unit 130 according to an embodiment of the present disclosure may be understood as a constituent unit that transmits and receives data through any type of known wired/wireless communication system. For example, the network unit 130 may perform data transmission and reception using a wired/wireless communication s a local area network (LAN), a wideband code division multiple access (WCDMA) network, a long term evolution (LTE) network, the wireless broadband Internet (WiBro), a 5th generation mobile communication (5G) network, a ultra wide-band wireless communication network, a ZigBee network, a radio frequency (RF) communication network, a wireless LAN, a wireless fidelity network, a near field communication (NFC) network, or a Bluetooth network. Since the above-described communication systems are only examples, the wired/wireless communication system for the data transmission and reception of the network unit 130 may be applied in various manners other than the above-described examples.

For example, the network unit 130 may receive an endoscopic image from an endoscope device, and may provide the detection results of the artificial neural network model to the endoscope device.

The data to be processed by the processor 110 may be stored in the memory 120 or received through the network unit 130, and the data generated by the processor 110 may be stored in the memory 120 or transmitted to the outside through the network unit 130.

Figure 2:
FIG. 2 is a block diagram of an artificial neural network model using training data according to one embodiment of the present disclosure.
Figure 3:
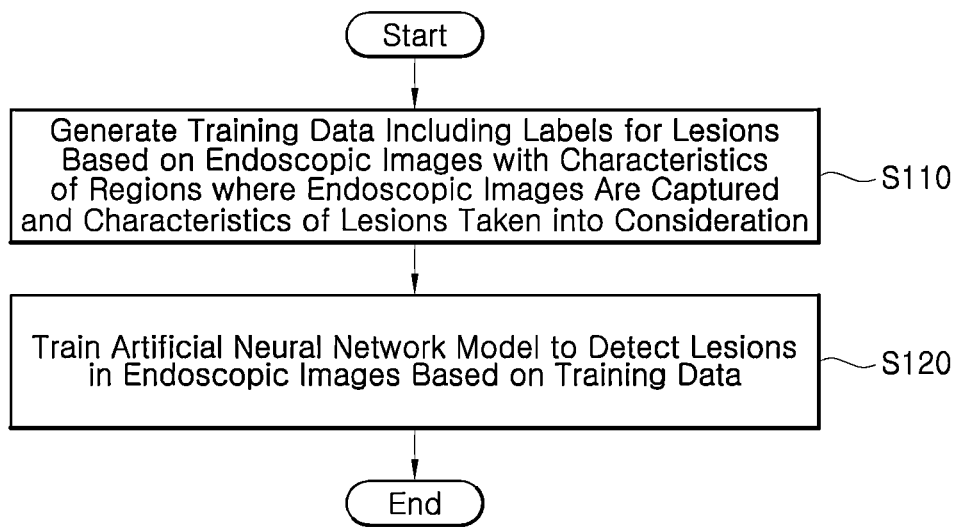
FIG. 3 is a flowchart showing a method by which a computing device trains an artificial neural network model according to one embodiment of the present disclosure.
Figure 4:
FIG. 4 is an exemplary view showing endoscopic images used as training data according to one embodiment of the present disclosure.
Figure 4:
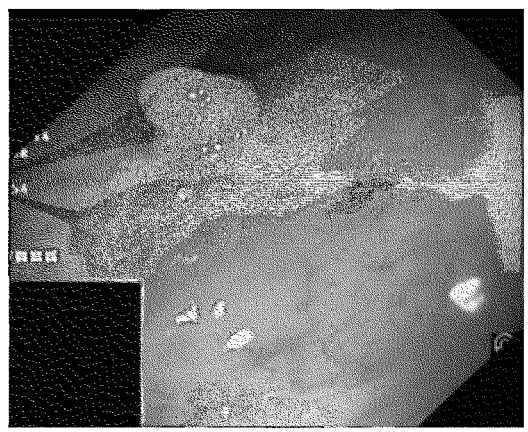
Figure 4:
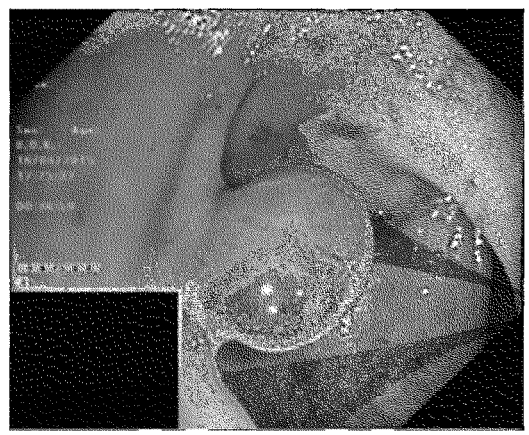
Figure 4:
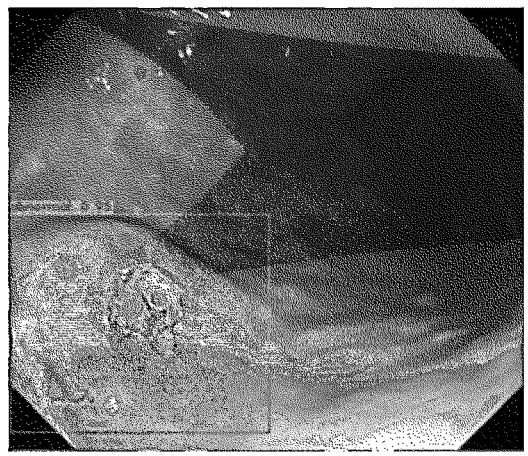

FIG. 2 is a block diagram of an artificial neural network model using training data according to one embodiment of the present disclosure, FIG. 3 is a flowchart showing a method by which a computing device trains an artificial neural network model according to one embodiment of the present disclosure, and FIG. 4 is an exemplary view showing endoscopic images used as training data according to one embodiment of the present disclosure.

Referring to FIGS. 1 to 4 together, the computing device 100 may generate training data 220 based on endoscopic images 210 to train the artificial neural network model 200. The trained artificial neural network model 200 may detect lesions or images not including a lesion in the endoscopic images 210.

The computing device 100 may generate the training data 220 including labels for lesions based on the characteristics of the regions where the endoscopic images 210 are captured and the characteristics of the lesions in step S110. More specifically, the computing device 100 may generate the training data 220 to include lesion training data including each of the lesions and normal training data not including any one of the lesions at a specific ratio. In this case, the ratio may be determined according to the clinical characteristics of the lesion. The clinical characteristics of the lesion may include the frequency of occurrence or type of the lesion.

For example, the computing device 100 may determine the ratio by taking into consideration the characteristics of a body region that is the target of an endoscopic procedure. For example, in the case of a gastroscope, the ratio between lesion training data and normal training data may be determined based on the type and incidence rate of a lesion occurring in the stomach. Furthermore, for the lesion training data, the ratio of the endoscopic images 210 including a lesion may be determined based on the incidence rate of the lesion according to the type of lesion. In this case, the determined ratio and the numbers of pieces of lesion training data and normal training data may not match. For example, the number of pieces of lesion training data may be insufficient. The computing device 100 may use a data augmentation technique to supplement the insufficient lesion training data 220. In this case, the computing device 100 may use an augmentation technique that maintains the image characteristics of lesions. For example, the computing device 100 may additionally generate endoscopic images by applying one or more image processing methods such as Rotation, Flipping, Crop, and/or Mosaic to the endoscopic images 210. Furthermore, there may not be used an augmentation technique that changes the characteristics of the endoscopic images 210, such as color, saturation, brightness, luminance, and/or the like, generated by the colors or light sources of the endoscopic images 210.

The computing device 100 may prepare learning data, verification data, and evaluation data based on the endoscopic images 210 for the training, verification, and evaluation of the artificial neural network model 200. That is, the training data 220 may include learning data, verification data, and evaluation data. In this case, the computing device 100 may construct the learning data, the verification data, and the evaluation data based on the patient information from which the training data 220 is obtained.

For example, the same patient information, i.e., the endoscopic images 210 generated from the same patient, may be constructed to pertain to any one of the groups of learning data, verification data, and evaluation data. The endoscopic images 210 obtained from the same patient may have similar image or clinical characteristics. When training, verification, and evaluation are performed using similar images, the accuracy of inference of the artificial neural network model 200 may be higher than intended. To prevent this, the data of the same patient may be included in one group.

The computing device 100 may train the artificial neural network model 200 to detect lesions in the endoscopic images 210 based on the training data 220 in step S120.

The artificial neural network model 200 may include at least one neural network. The neural network may include network models such as a deep neural network (DNN), a recurrent neural network (RNN), a bidirectional recurrent deep neural network (BRDNN), a multilayer perceptron (MLP), a convolutional neural network (CNN), and a transformer, but is not limited thereto.

The computing device 100 may train the artificial neural network model 200 through supervised learning that uses the training data 220 as input values. Alternatively, the artificial neural network model 200 may be trained through unsupervised learning that discovers criteria for data recognition by learning the types of data required for data recognition on its own without any guidance. Alternatively, the artificial neural network model 200 may be trained through reinforcement learning that uses feedback on whether the results of data recognition according to learning are correct.

For example, the artificial neural network model 200 of the present disclosure may be constructed as an architecture based on a one-step detection algorithm. The artificial neural network model 200 may include a backbone configured to extract features from the input training data 220 and classify the features, and a detector configured to detect an object. The detector includes a loss function adapted to predict the coordinates of a bounding box. In this case, the computing device 100 may determine the type of loss function of the artificial neural network model 200 to increase the accuracy of lesion detection, specifically to increase the accuracy of a bounding box. That is, the computing device 100 may determine the loss function of the artificial neural network model 200 according to the clinical or image characteristics of the lesion.

For example, the type of loss function may include a generalized intersection over union (GIoU) loss function designed to consider the distance between two objects while maintaining the property of not changing the scale based on the intersection over union (IoU) between overlapping objects, a distance IoU (DIoU) loss function designed to improve the convergence speed by adding a term for a penalty corresponding to the center point distance between two objects to the GIoU loss function, and a complete IoU (CIoU) loss function designed to enable faster convergence when objects do not overlap by adding a penalty term for the consideration of the aspect ratio between two objects to the DIoU loss function.

The artificial neural network model 200 of the present disclosure may use a loss function having a DIoU structure as its loss function. In the case of lesion training data, a bounding box including a lesion may include a plurality of lesions. Alternatively, depending on the direction of the scope that obtains each of the endoscopic images 210, the direction of the image in which a lesion is captured may change, and thus, the aspect ratio of the bounding box may change. Accordingly, the aspect ratio of the bounding box is unlikely to be a factor that improves the accuracy of lesion detection.

The computing device 100 may train the artificial neural network model 200 to detect images not including a lesion in the endoscopic images 210 based on the training data 220. In an actual endoscopic procedure, the rate at which endoscopic images 210 not including a lesion are detected may be higher than the rate at which endoscopic images 210 including a lesion are detected. Accordingly, it is important for the artificial neural network model 200 to secure the accuracy of detecting the endoscopic images 210 not including a lesion as well as the accuracy of detecting the endoscopic images 210 including a lesion.

To this end, the computing device 100 may use the endoscopic images 210 not including a lesion and not having a bounding box, such as that shown in FIG. 4(a), as the training data 220. Furthermore, the computing device 100 may design a loss function based on a loss function for detecting lesions and a loss function for detecting images not including a lesion so that the artificial neural network model 200 can detect lesions or images not including any of the lesions, and may then use the designed loss function for training.

The computing device 100 may train the artificial neural network model 200 by assigning weights so that the inference results of the artificial neural network model 200 are determined by reflecting the clinical characteristics of lesions therein. For example, the computing device 100 may assign a higher weight to training data 220 including a lesion with higher difficulty in reading. The difficulty in reading may be determined according to image characteristics indicating the frequency of occurrence, form, color, shape, size and/or like of the lesion and the information of the patient from whom the corresponding endoscopic image 210 is obtained.

Referring to FIG. 4 as an example, FIGS. 4(b) and 4(c) show endoscopic images 210 including a pedunculated polyp. In contrast, FIG. 4(d) shows an endoscopic image 210 including a pedunculated or flat polyp. Since a flat polyp has a flat shape, there is a high possibility that an endoscope operator will miss the detection thereof. To prevent this, the artificial neural network model 200 needs to detect this type of lesion with higher sensitivity than a lesion having low reading difficulty. Accordingly, the computing device 100 may use separate weights for lesions having high reading difficulty.

Figure 5:
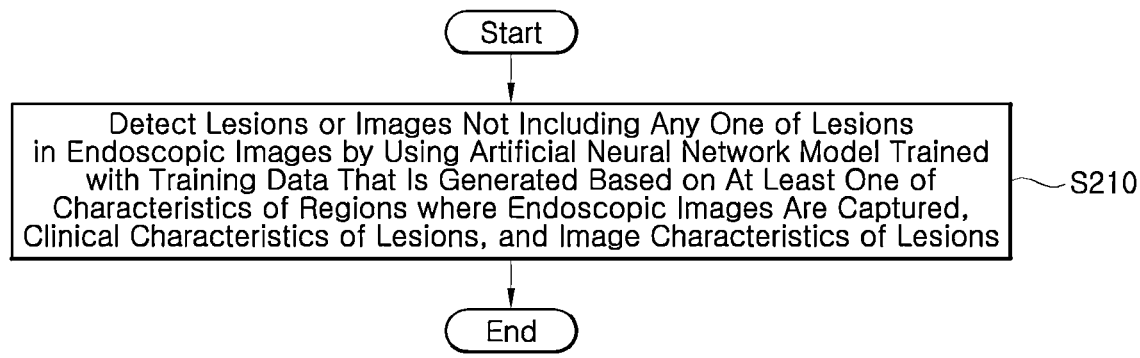
FIG. 5 is a flowchart showing the operation of an artificial neural network model according to one embodiment of the present disclosure.

FIG. 5 is a flowchart showing the operation of an artificial neural network model according to one embodiment of the present disclosure.

Referring to FIGS. 2 and 5, the computing device 100 may detect lesions or images not including a lesion in the endoscopic images 210 by using the artificial neural network model 200 trained with the training data 220 that is generated based on at least one of the characteristics of the regions where the endoscopic images 210 are captured, the clinical characteristics of lesions, and the image characteristics of the lesions in step S210. The computing device 100 may receive the endoscopic images 210 from the endoscope device, may infer the presence or absence of a lesion, and may provide inference results to the endoscope device.

Furthermore, the computing device 100 may use an object detection model together with the trained artificial neural network model 200. The object detection model may track a bounding box that includes a lesion detected by the artificial neural network model 200. This may provide smoother detection results in real-time images while an endoscopic procedure is performed.

The various embodiments of the present disclosure described above may be combined with one or more additional embodiments, and may be changed within the scope understandable to those skilled in the art in light of the above detailed description. The embodiments of the present disclosure should be understood as illustrative but not restrictive in all respects. For example, individual components described as unitary may be implemented in a distributed manner, and similarly, components described as distributed may also be implemented in a combined form. Accordingly, all changes or modifications derived from the meanings and scopes of the claims of the present disclosure and their equivalents should be construed as being included in the scope of the present disclosure.

What is claimed is:

1. A method of training an artificial neural network model for detecting lesions in endoscopic images, the method being performed by a computing device including at least one processor, the method comprising:
   generating training data including labels for lesions based on endoscopic images with characteristics of regions where the endoscopic images are captured and characteristics of the lesions taken into consideration; and
   training an artificial neural network model to detect the lesions in endoscopic images based on the training data, wherein, assigning weights so that inference results of the artificial neural network model are determined by reflecting clinical characteristics of the lesions therein, assigning higher weights to training data including a lesion with higher reading difficulty,
   wherein generating the training data comprises generating the training data such that a number of lesion training data including each of the lesions is less than a number of normal training data not including the lesion, by considering a ratio of the lesion training data and the normal training data,
   wherein a loss function of the artificial neural network model includes a loss function having a structure that does not consider an aspect ratio of a bounding box for the lesion, and is determined according to the clinical characteristics or image characteristics of the lesions.

2. The method of claim 1, wherein:
   the ratio of the lesion training data and the normal training data is determined according to the clinical characteristics of the lesions.

3. The method of claim 2, wherein the clinical characteristics of the lesions include a frequency of occurrence or type of the lesions.

4. The method of claim 2, wherein the lesion training data is generated by an augmentation technique that maintains the image characteristics of the lesions.

5. The method of claim 1, wherein:
the training data includes learning data, verification data, and evaluation data; and
the learning data, the verification data, and the evaluation data are constructed based on patient information from which the training data is obtained.

6. The method of claim 1, wherein the loss function of the artificial neural network model includes a loss function having a distance IoU (DIoU) structure.

7. The method of claim 1, wherein the artificial neural network model is trained to detect images not including any one of the lesions in endoscopic images based on the training data.

8. The method of claim 7, wherein the loss function of the artificial neural network model is determined based on a loss function adapted to detect the lesions and a loss function adapted to detect images not including any one of the lesions.

9. A method of detecting lesions in endoscopic images, the method being performed by a computing device including at least one processor, the method comprising:
detecting lesions or images not including any one of the lesions in endoscopic images by using an artificial neural network model trained with training data that is generated based on at least one of characteristics of regions where endoscopic images are captured, clinical characteristics of the lesions, and image characteristics of the lesions,
wherein the artificial neural network model assigns weights so that inference results of the artificial neural network model are determined by reflecting the clinical characteristics of the lesions therein, and assigns higher weights to the training data including a lesion with higher reading difficulty,
wherein the training data includes lesion training data including each of the lesions and normal training data not including the lesion, and is generated by considering a ratio of the lesion training data and the normal training data, a number of the lesion training data is less than a number of the normal training data,
wherein a loss function of the artificial neural network model includes a loss function having a structure that does not consider an aspect ratio of a bounding box for the lesion, and is determined according to the clinical characteristics or the image characteristics of the lesions.

10. A computing device for training an artificial neural network model for detecting lesions in endoscopic images, the computing device comprising:
a processor including at least one core; and
memory including program codes executable on the processor;
wherein the processor generates training data including labels for lesions based on endoscopic images with characteristics of regions where the endoscopic images are captured and characteristics of the lesions taken into consideration, and trains an artificial neural network model to detect the lesions in endoscopic images based on the training data,
wherein the processor assigns weights so that inference results of the artificial neural network model are determined by reflecting clinical characteristics of the lesions therein, and assigns higher weights to training data including a lesion with higher reading difficulty,
and generates the training data such that a number of lesion training data including each of the lesions is less than a number of normal training data not including the lesion, by considering a ratio of the lesion training data and the normal training data,
wherein a loss function of the artificial neural network model includes a loss function having a structure that does not consider an aspect ratio of a bounding box for the lesion, and is determined according to the clinical characteristics or image characteristics of the lesions.

* * * * *